United States Patent [19]

Kump et al.

[11] Patent Number: 5,147,870
[45] Date of Patent: Sep. 15, 1992

[54] SUBSTITUTED AZACYCLOHEXYL DERIVATIVES

[75] Inventors: Wilhelm Kump, Biel-Benken, Switzerland; Keith A. Menear, Horsham, England

[73] Assignee: Ciba-Geigy Corporation, Ardsley, N.Y.

[21] Appl. No.: 781,638

[22] Filed: Oct. 18, 1991

Related U.S. Application Data

[63] Continuation of Ser. No. 392,625, filed as PCT/CH88/00198, Oct. 21, 1988, abandoned.

[30] Foreign Application Priority Data

Oct. 27, 1987 [GB] United Kingdom ............... 8725118
Jun. 30, 1988 [CH] Switzerland ............... 2500/88-3

[51] Int. Cl.$^5$ ............... C07D 521/00; A61K 31/395
[52] U.S. Cl. ............... 514/783; 514/255; 340/468; 544/368
[58] Field of Search ............... 540/468; 344/368; 514/183; 314/255

[56] References Cited

U.S. PATENT DOCUMENTS

| | | | |
|---|---|---|---|
| 4,005,077 | 1/1977 | Bickel et al. | 260/239.3 |
| 4,327,096 | 4/1982 | Marsili et al. | 424/250 |
| 4,353,826 | 10/1982 | Bickel et al. | 260/239.3 |
| 4,876,258 | 10/1989 | Kump et al. | 514/524 |
| 4,916,126 | 4/1990 | Traxler et al. | 514/183 |
| 4,918,066 | 4/1990 | Kump | 514/183 |
| 5,003,070 | 3/1991 | Kump et al. | 544/368 |
| 5,053,510 | 10/1991 | Kump | 544/368 |

FOREIGN PATENT DOCUMENTS

| | | | |
|---|---|---|---|
| 314041 | 5/1989 | European Pat. Off. | 540/468 |
| 350445 | 1/1990 | European Pat. Off. | 544/368 |
| 8702361 | 4/1987 | World Int. Prop. O. | 540/468 |

| | | | |
|---|---|---|---|
| WO87/3834 | 10/1988 | World Int. Prop. O. | 544/368 |

OTHER PUBLICATIONS

Burger's Med. Chem. 4th Ed. part III pp. 320, 321 & 577, John Wiley & Sons, New York 1979.
Taguchi et al., Chem. Pharma. Bull. vol. 33, No. 5 pp. 2133-2136 (1965).

*Primary Examiner*—Robert T. Bond
*Attorney, Agent, or Firm*—Norbert Gruenfeld; JoAnn Villamizar

[57] ABSTRACT

The invention relates to the preparation of substituted azacyclohexyl derivatives of rifamycins of the formula

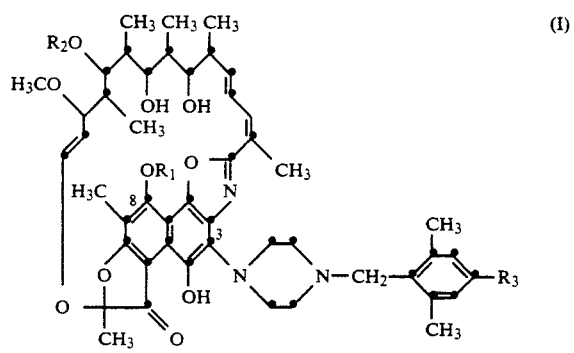

and salts thereof in which $R_1$ is hydrogen or trialkylacetyl, $R_2$ is hydrogen or acetyl and $R_3$ is alkyl, which exhibit valuable pharmacological properties.

11 Claims, No Drawings

SUBSTITUTED AZACYCLOHEXYL DERIVATIVES

This application is a continuation, of application Ser. No. 392,625, filed Jun. 20, 1989 now abandoned (PCT/CH88/00198 filed Oct. 21, 1988).

The present invention relates to novel substituted azacyclohexyl derivatives of rifamycins of formula

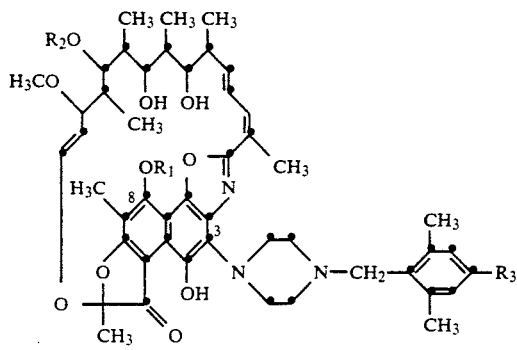

and salts thereof in which $R_1$ is hydrogen or trialkylacetyl, $R_2$ is hydrogen or acetyl and $R_3$ is alkyl, to their preparation and use and to pharmaceutical preparations and the manufacture thereof.

The numbering of the ring system corresponds to that used, for example, in U.S. Pat. No. 4,005,077.

The compounds of formula I contain a number of chirality centres, and accordingly the present invention also includes the corresponding optical isomers, for example diastereoisomers.

The compounds of formula I may be in the form of salts, especially pharmaceutically acceptable salts. As the compounds of this invention contain basic centres they are able to form acid addition salts. Such salts are formed, for example, with inorganic acids, such as mineral acids, for example sulfuric acid, a phosphoric or hydrohalic acid, or with organic carboxylic acids, such as $C_1$-$C_4$alkane-carboxylic acids that are unsubstituted or substituted, for example, by halogen, for example acetic acid; unsaturated or saturated dicarboxylic acids, for example oxalic, malonic, succinic, maleic, fumaric, phthalic or terephthalic acid; hydroxycarboxylic acids, for example glycolic acid, lactic acid, malic acid, tartaric acid or citric acid; amino acids, for example aspartic acid or glutamic acid; or with organic sulfonic acids, such as unsubstituted or, for example, halogen-substituted, $C_1$-$C_4$alkane- or aryl-sulfonic acids, for example methane-sulfonic acid, bromobenzenesulfonic acid or toluenesulfonic acid. Corresponding acid addition salts can also be formed with the additionally present basic centre. Further, the compounds of the invention containing an acid phenolic hydroxyl group can form salts with bases, for example alkali metal salts, such as sodium or potassium salts. In addition, corresponding internal salts can be formed. Salts which are unsuitable for pharmaceutical purposes are also included, since these salts can be used, for example, for the isolation and purification of compounds of the invention or the pharmaceutically acceptable salts thereof.

Trialkylacetyl is especially tri-$C_1$-$C_7$alkylacetyl, preferably tri-$C_1$-$C_4$alkylacetyl, in which alkyl is in each case as defined hereinafter. Pivaloyl is most preferred Alkyl is especially $C_1$-$C_7$alkyl and is, for example, methyl, ethyl, propyl, isopropyl, n-butyl, isobutyl, sec.-butyl, tert.-butyl, and further comprises corresponding pentyl, hexyl and heptyl radicals. $C_1$-$C_4$alkyl, especially methyl, is preferred.

Derivatives that are derived, for example, from rifamycin SV, are known to have pronounced antibiotic properties and can be used, for example, for the treatment of tuberculosis. The finding, verified by experiments, that the compounds of formula I and the pharmaceutically acceptable salts thereof do not exhibit any corresponding antibiotic activity in the conventional pharmacological test models for assessment, is therefore all the more surprising.

Surprisingly, however, they do have a significant lipid-lowering activity, which can be demonstrated in animal tests, preferably carried out on mammals, for example rats. Thus, the lowering of very low density, low density and high density lipoproteins (VLDL, LDL and HDL) in serum can be demonstrated in two test procedures in male rats with genetic hypercholesterolaemia (procedure A) and in normolipaemic rats of both sexes (procedure B).

Albino rats having a body weight of 180–240 g and with free access to standard rat feed and drinking water are used. The rats are Sprague Dawley progeny of the COBS strain. The test compound is administered orally to groups of 8 to 10 rats, daily for 5 consecutive days, in a 3 % corn starch solution. Two hours after the last administration the animals are sacrificed by being bled by cardiac puncture under anaesthesia with carbon dioxide. For a period of 16 hours before being sacrificed the animals receive no more food. The total cholesterol, lipoprotein and triglyceride blood plasma levels are determined separately for each test animal. In order to determine the lipoproteins the VLDL and LDL fractions are precipitated from 1 ml of ethylenediaminetetraacetic acid anticoagulated plasma by the addition of 200 units of heparin and manganese chloride to a final concentration of 46 mmol/litre and centrifuged off.

The supernatant solution is combined with the remaining plasma and analysed enzymatically for their content of cholesterol and triglycerides using test systems supplied, for example, by Sigma Chemical Co. (St. Louis, Mo., USA).

The test for antibiotic activity is carried out, for example, on the one hand in vitro by determining the minimum inhibitory concentration (MIC) in the conventional plate test. The microorganisms used for this purpose are especially Mycobacterium tuberculosis TB $H_{37}Rv$ and Staphylococcus aureus. When using compounds having a lipid-lowering indication, an antibiotic activity is considered a disadvantage, as it can lead to the formation of strains of microorganisms that are resistant to antibiotics, especially in the case of long-term administration.

In the above-described test methods, the compounds of the invention, when administered repeatedly in the dosage range of from about 1 to about 10 mg/kg per day, exhibit a significant hypolipidaemic activity. Thus, for example, it can be shown that, depending on the test procedure, the minimum effective dose of the compounds of the invention when administered in a single dose is from about 1 to about 3 mg/kg, and that a 75 % lowering of the LDL fraction can be achieved by repeated administration of 10 mg/kg daily. Surprisingly, the compounds prepared in accordance with the invention have virtually no antibiotic activity; the MIC for various pathogenic strains of Staphylococcus aureus, for example, is higher than 130 μg/ml. Such values are about 1000 times higher than concentrations normally required for a corresponding effect.

Especially on account of their LDL-lowering activity, the compounds of this invention can b=used, for example, as hypolipidaemic agents for the treatment of hyperlipidaemiae, mainly of types IIa and IIb, and arteriosclerosis, for example when hyperlipoproteinaemia is a risk factor.

Accordingly, the compounds of formula I and the pharmaceutically acceptable salts thereof can be used, for example, as pharmaceutical agents' for example as hypolipidaemic, agents for the treatment of hyperlipidaemiae, mainly of types IIa and IIb, and of arteriosclerosis when hyperlipoproteinaemia is a risk factor. The invention further relates to the use of the compounds of the invention for the preparation of medicaments, especially hypolipidaemic agents and antiarteriosclerosis agents, and for therapeutic and prophylactic treatment. The commercial manufacture of the active substances also falls within the scope of this invention.

The invention relates especially to compounds of formula I and salts thereof in which $R_1$ is pivaloyl and $R_3$ is methyl.

The invention relates especially to the novel compounds described in the Examples and to the preparation thereof.

The invention further relates to processes for the preparation of the compounds of the invention. The preparation of compounds of formula I and salts thereof is carried out in a manner known per se and comprises, for example, reacting a compound of the formula

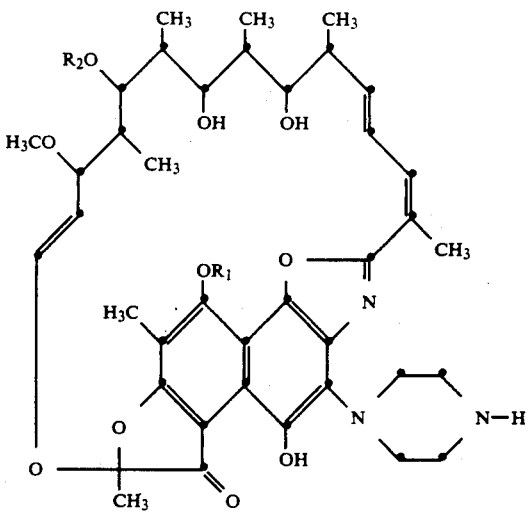

or a salt thereof with a compound of formula

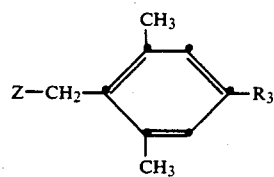

wherein Z is reactive esterified hydroxy, or b) for the preparation of compounds of formula I and salts thereof in which $R_1$ is trialkylmethylcarbonyl and $R_2$ is acetyl, heating a compound of formula

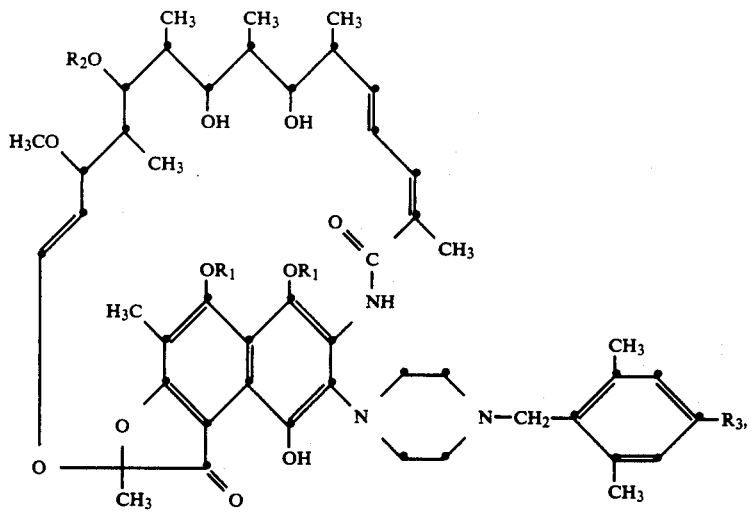

or c) heating or irradiating a compound of formula

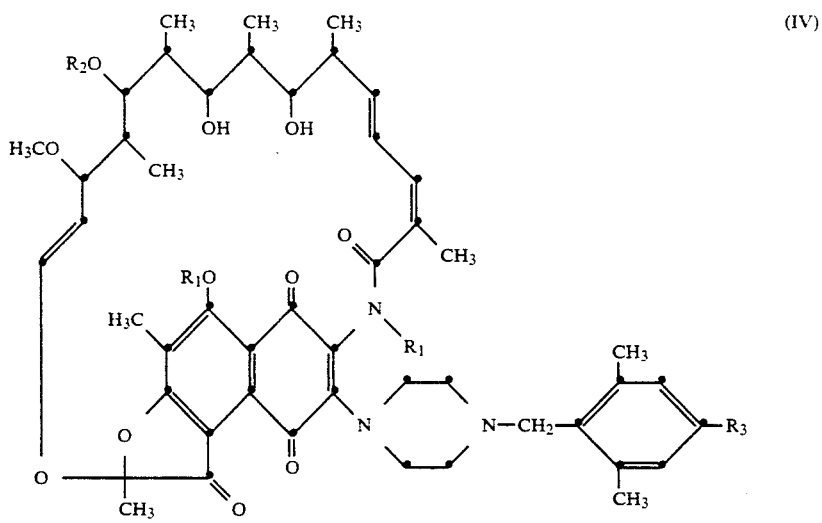

and, if desired, converting a compound of formula I obtainable by the process or in another manner, or a salt thereof, into a different compound of the invention or a salt thereof, or converting a free compound of formula I obtainable by the process into a salt and/or a salt obtainable by the process into the free compound of formula I or into a different salt.

Salts of the starting materials of formulae IIa, III and IV that contain an acid phenolic hydroxy group are corresponding salts with bases of the kind indicated hereinbefore, whereas corresponding starting compounds with basic centres can also form corresponding acid addition salts similar to the acid addition salts of formula I.

Reactive esterified hydroxy is especially hydroxy esterified with a strong inorganic acid or organic sulfonic acid, and is, for example, halogen, such as chlorine, bromine or iodine, sulfonyloxy, such as hydroxysulfonyloxy, halosulfonyloxy, for example fluorosulfonyloxy, $C_1$-$C_7$-alkanesulfonyloxy that is unsubstituted or substituted, for example, by halogen, for example methanesulfonyloxy or trifluoromethanesulfonyloxy, $C_5$-$C_7$cycloalkanesulfonyloxy, for example cyclohexanesulfonyloxy, or benzenesulfonyloxy that is unsubstituted or substituted, for example, by $C_1$-$C_7$alkyl or halogen, for example p-bromobenzenesulfonyloxy or p-toluenesulfonyloxy.

The reactions described hereinbefore and hereinafter in the variants are carried out in a manner known per se, for example in the absence or, normally, in the presence, of a suitable solvent or diluent or a mixture thereof, the process being carried out, as required, with cooling, at room temperature or with heating, for example in a temperature range of approximately from −80° to the boiling temperature of the reaction medium, preferably from about −10° to about +180° C. and, if necessary, in a closed vessel, under pressure, in an inert gas atmosphere and/or under anhydrous conditions.

The working up of the reaction product from the reaction mixture obtainable in accordance with the process is effected in a manner known per se, for example by dilution with water and/or, if desired, by neutralisation or slight acidification (to about pH 3) with an aqueous acid, such as an inorganic or organic acid, for example a mineral acid or, advantageously, citric acid, and the addition of a water-immiscible solvent, such as a chlorinated hydrocarbon, for example chloroform or methylene chloride, the reaction product passing into the organic phase from which it can be obtained in purified form in conventional manner, for example by drying, concentrating the solvent by evaporation, and crystallisation and/or chromatography of the residue, or by other customary methods of purification.

Variant a):

Z is preferably halogen, such as chlorine, bromine or iodine, as well as sulfonyloxy, such as methanesulfonyloxy or p-toluenesulfonyloxy.

The reaction is conducted in a manner known per se, advantageously in the presence of a base.

Suitable bases are preferably non-nucleophilic tertiary amines, for example tri-lower alkylamines, basic heterocycles and carbocyclic amines, such as ethyl diisopropylamine, triethylamine, pyridine, 1,5-diazabicyclo[4.3.0]non-5-ene (DBN), as well as 1,8-diazabicyclo[5.4.0]undec-7-ene (DBU).

Variant b):

The treatment of compounds of formula III is carried out with heating, for example in a temperature range of approximately from 50° to 180° C., especially approximately from 100° to 170° C.

The starting material of formula III can be prepared, for example, by reacting rifamycin S or 3-halo-rifamycin S, especially 3-bromo-rifamycin S, with an amine of formula

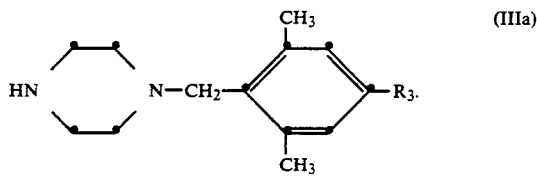

The reaction is carried out especially with an excess of the amine of formula IIIa, for example in a temperature range of from about 0° to about 100° C., a mixture of the quinone and hydroquinone form being formed. This mixture can be converted into the corresponding hydroquinone (derivative of rifamycin SV) by reduction, for example by catalytic hydrogenation ($R_1$=H). By treatment with corresponding acylating agents, for example with an acid anhydride, such as pivaloyl chloride, in the presence of a base, such as pyridine, compounds of formula III in which R₁ is trialkylacetyl can be obtained.

Variant c):

The reaction is carried out especially in an organic solvent, for example an alcohol, such as methanol, ethanol or isopropanol, a ketone, such as acetone or methyl ethyl ketone, a chlorinated hydrocarbon, such as chloroform or trichloroethane, an ether, such as diethyl ether, a base, such as pyridine or triethylamine, or a nitrile, such as acetonitrile. Preferred solvents are isopropanol and pyridine.

If the temperature is too low, the reaction proceeds very slowly, whereas at too high a temperature substantial amounts of unwanted by-product are formed A suitable temperature range is from about 50° to about 90° C., preferably about 75° C.

Irradiation is carried out in a manner known per se, for example using conventional sources of irradiation, such as microwave irradiation.

The resulting product can be purified and isolated, for example by chromatography and/or recrystallisation from a suitable solvent, such as petroleum ether.

The starting material of formula IV can be prepared in a manner known per se, for example by treating a compound of formula quinoline, a tertiary amine, for example triethylamine, N-ethylpiperidine, N-methylmorpholine or 1,4-dimethylpiperazine, or 1,5-diazabicyclo[5.4.0]undec-5-ene.

The acylation is normally carried out in the presence of a solvent or diluent, using also an excess of the acylating agent or of the base, for example pyridine, together with an acylating agent. Other solvents which, for example, can also be used in admixture with a base, are, for example, non-acylatable organic solvents, such as hydrocarbons, for example pentane, hexane or cyclohexane, halogenated hydrocarbons, for example methylene chloride or chloroform, ethers, for example diethyl ether, ethylene glycol dimethyl ether, tetrahydrofuran or dioxane, acid esters, such as ethyl acetate, and acid amides, for example acetamide or dimethylformamide.

The reaction is normally carried out at room temperature or at slightly elevated temperature, for example up to about 70° C., and, if necessary, in an inert gas atmosphere. The acylation conditions, especially the amount of acylating agent used, the reaction medium, the temperature and the reaction time, should be so chosen that both acyl groups are introduced, the procedure used preferably being as described in detail in the Examples. The course of the reaction may advantageously be monitored by means of customary analytical methods, especially by thin-layer chromatography.

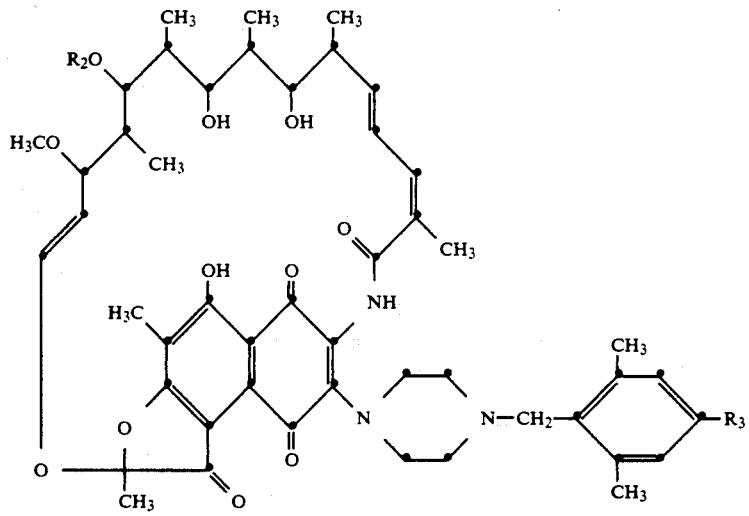

(IVa)

with an acylating reagent that introduces the trialkylacetyl group in positions 8 and 14.

The trialkylacetyl group can be introduced in a manner known per se with a suitable acylating agent, using at least two equivalents of the latter. It is possible to use, for example, a corresponding carboxylic acid, if necessary in the presence of a suitable condensing agent, such as dicyclohexylcarbodiimide, but preferably a reactive derivative of such an acid, such as an anhydride, especially a mixed anhydride, for example one with an inorganic acid, such as a hydrohalic acid, especially hydrochloric acid or hydrobromic acid (that is to say, a corresponding acid halide, for example an acid chloride), or with an organic acid, such as (trifluoro-)acetic acid or a suitable monoester of carbonic acid, or alternatively a symmetric anhydride, or an inner anhydride, that is to say the corresponding ketene. The carboxylic acid derivative employed as acylating agent is preferably used in the presence of a basic agent. A suitable basic agent is especially a non-acylatable organic base, such as a heteroaromatic base, for example pyridine, collidine or The starting material of formula IVa is known or can be prepared in a manner known per se, in which connection reference is made especially to the PCT Application published under the number WO 87/02361.

The invention further relates to the novel compounds obtainable by the above-described process variants.

A compound of formula I obtainable in accordance with the invention or in another manner, or a salt thereof, can be converted in a manner known per se into a different compound of formula I.

Compounds of formula I in which R₁ is hydrogen can be acylated in a manner known per se, for example by reaction with the appropriate carboxylic acid or a reactive derivative thereof. Such reactive derivatives are, for example, anhydrides, including mixed anhydrides, such as an acid halide, for example an acid chloride, or anhydrides with a formic acid ester, activated carboxylic acid esters, such as cyanomethyl ester, (4-)nitrophenyl ester, and polyhalophenyl esters, for example pentachlorophenyl ester. The reaction with the carboxylic acid or a salt thereof is carried out with removal of water, for example azeotropic removal of the water of reaction, or by treatment with a suitable condensing agent, for example N,N'-dicyclohexylcarbodiimide. The reaction with a reactive acid derivative is advantageously carried out in the presence of a base. Similarly, the acetyl radical $R_2$ can be introduced into compounds of formula I in which $R_2$ is hydrogen by treatment with a suitable acetylating agent.

The acetyl radical $R_2$ and the acyl radical $R_1$ can be replaced by hydrogen by treatment with strong bases, such as alkali metal hydroxides. The acyl radical $R_1$ can also be removed selectively in the presence of the acetyl radical $R_2$, for example by treatment with a fluoride, such as an alkali metal fluoride, for example sodium or caesium fluoride, or with an ammonium fluoride, for example tetrabutylammonium fluoride.

Salts of compounds of formula (I) can be prepared in a manner known per se. Thus, for example, acid addition salts of compounds of formula (I) are obtained by treatment with an acid or with a suitable ion exchange reagent. Salts can be converted in customary manner into the free compounds; acid addition salts, for example, by treatment with a suitable basic agent.

Depending on the procedure and on the reaction conditions, the compounds of the invention having salt-forming, especially basic, properties, can be obtained in free form or, preferably, in the form of salts.

Owing to the close relationship between the novel compound in free form and in the form of its salts, hereinbefore and hereinafter references to the free compound or its salts shall also, where appropriate with regard to context, include the corresponding salts or the free compound respectively.

The novel compounds, including their salts of salt-forming compounds, can also be obtained in the form of hydrates or include other solvents used for crystallisation.

Depending on the choice of starting materials and procedures, the novel compounds may be in the form of one of the possible isomers or in the form of mixtures thereof, for example depending on the number of asymmetric carbon atoms they may be in the form of pure optical isomers, such as antipodes, or in the form of mixtures of isomers, for example racemates, mixtures of diastereoisomers or mixtures of racemates.

Resulting mixtures of racemates can be separated in known manner into the pure isomers or racemates on the basis of the physico-chemical differences between the components, for example by fractional crystallisation.

Resulting racemates can also be resolved into the optical antipodes by known methods, for example by recrystallisation from an optically active solvent, chromatography on chiral adsorbents, with the aid of suitable microorganisms, by cleavage with specific immobilised enzymes, via the formation of inclusion compounds, for example using chiral Crown ethers, only one enantiomer being complexed, or by conversion into diastereoisomeric salts, for example by reaction of a basic end product racemate with an optically active acid, such as a carboxylic acid, for example tartaric or malic acid, or a sulfonic acid, for example camphorsulfonic acid, and separation of the resulting mixture of diastereoisomers, for example on the basis of their different solubilities, into the diastereoisomers from which the desired enantiomers can be freed by the action of suitable agents. It is advantageous to isolate the more active enantiomer.

The invention also relates to those embodiments of the process in which a compound obtainable as intermediate at any stage of the process is used as starting material and the remaining steps are carried out, or a starting material is used in the form of a derivative or salt and/or its racemates or antipodes or, especially, is formed under the reaction conditions.

In the process of this invention it is preferred to use those starting materials that lead to the compounds referred to at the outset as being especially valuable. The invention further relates to novel starting materials that have been specially developed for the preparation of the compounds of the invention, especially novel compounds of formula III, their use, and processes for their preparation, the variables $R_1$, $R_2$ and $R_3$ having the meanings given for the respective preferred groups of compounds of formula I.

The present invention also relates to the use of compounds of formula I and salts thereof alone or together with adjuncts, as well as in conjunction with other active substances, as agents for the therapeutic treatment, that is the curative as well as preventive treatment, of diseases or pathological conditions that are indicated or caused, for example, by an increased content of chlolesterol and/or triglycerides in blood, especially in blood serum. The active ingredients of the invention are administered to the warm-blooded animals requiring treatment, primarily humans, in therapeutically effective amounts, preferably in the form of pharmaceutical compositions together with conventional pharmaceutical carriers and/or adjuncts. Depending on the species, body weight, age and individual condition, for example daily doses of about 1 to about 100, preferably of about 3 to about 50, mg/kg of body weight, which doses may be exceeded in acute cases, are administered to warm-blooded animals. The invention also relates by analogy to the corresponding method of medical treatment.

The invention further relates to pharmaceutical preparations that contain the compounds of the invention or pharmaceutically acceptable salts thereof as active ingredients, and to processes for the preparation thereof.

The pharmaceutical preparations of the invention, which contain the compound of the invention or pharmaceutically acceptable salts thereof, are for enteral, such as oral or also rectal, and parenteral administration to warm-blooded animals, and contain the pharmacological active ingredient on its own or together with a pharmaceutically acceptable carrier.

The novel pharmaceutical preparations contain, for example, from about 10% to about 80%, preferably from about 20% to about 60%, of the active ingredient. Pharmaceutical preparations of the invention for enteral or parenteral administration are, for example, those in dosage unit forms, such as dragees, tablets, capsules or suppositories, as well as ampoules. These pharmaceutical preparations are prepared in a manner known per se, for example by conventional mixing, granulating, confectioning, dissolving or lyophilising methods. For example, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragee cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, and/or polyvinylpyrrolidone, if desired disintegrators, such as the above-mentioned starches, also carboxymethyl starch, crosslinked polyvinylpyrrolidone, agar, or alginic acid or a salt thereof, such as sodium alginate. Adjuncts are especially flow agents, flow-regulating agents and lubricants, for example silicic acid, talc, stearic acid or salts thereof, such as magnesium or calcium stearate, and/or polyethylene glycol. Dragee cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or dragee coatings, for example for the purposes of identification or to indicate different doses of active ingredient.

Other orally administrable pharmaceutical preparations are dry-fill capsules made of gelatin, and also soft, sealed capsules made of gelatin and a plasticiser, such as glycerol or sorbitol. The dry-filled capsules may contain the active ingredient in the form of a granulate, for example in a mixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules that contain a combination of the active ingredient with a base material. Suitable base materials are, for example, liquid triglycerides, polyethylene glycols or paraffin hydrocarbons.

There are suitable for parenteral administration especially aqueous solutions of an active ingredient in water-soluble form, for example a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions that contain viscosity-increasing substances, for example sodium carboxymethylcellulose, sorbitol and/or dextran, and, where appropriate, also stabilisers.

The dosage of the active ingredient depends on the species of warm-blooded animal, the age and individual condition, as well as on the mode of application. Normally, an approximate daily dose of about 150 mg to about 1500 mg, advantageously in several equal partial doses, is proposed in the case of oral administration to a warm-blooded animal weighing about 75 kg.

The following Examples illustrate the above-described invention, but in no way limit the scope thereof.

EXAMPLE 1

30 g of 1,8-di-O-pivaloyl-3-[4-(2,4,6-trithylbenzyl)piperazin-1-yl]-rifamycin SV are dissolved, with the application of heat, in 1000 ml of 2-methoxyethanol and the solution is refluxed for 5 hours under nitrogen. The solvent is then concentrated by evaporation under vacuum and the residue is crystallised twice from methanol, yielding 8-O-pivaloyl-1-deoxy-15-deoxo-1,15-oxy-3-[4-(2,4,6-trimethylbenzyl)piperazin-1-yl]-rifamycin of formula I in which $R_1$ is pivaloyl, $R_2$ is acetyl and $R_3$ is methyl. Melting point 160°–165° C.

$C_{56}H_{73}N_3O_{12}$; M=979, found (MS): 979; $^1$H-NMR (360 MHz, CDCl$_3$, TMS): 1.49 (s, 9 H, pivaloyl at 0–8).

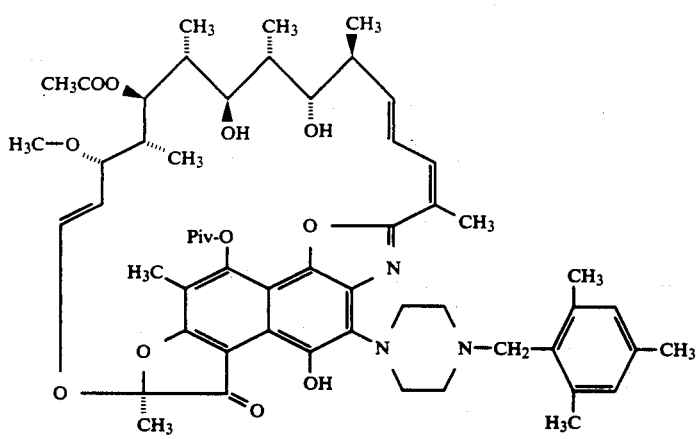

Piv = pivaloyl—.

The starting material can be prepared as follows: A mixture of 5 g of 3-[4-(2,4,6-trimethylbenzyl)piperazin-1-yl]-rifamycin SV, 50 ml of dry pyridine and 4.5 ml of pivaloyl chloride is kept at 50° C. for 30 minutes. The solvent is then evaporated under vacuum. The oily residue is dissolved in ethyl acetate and the solution is washed with 2N hydrochloric acid, with a buffer solution of pH 7, and with a solution of sodium chloride The whole is dried over sodium sulfate and concentrated by evaporation and the yellow residue is crystallised from ether/hexane, yielding 1,8-di-O-pivaloyl-3-[4-(2,4,6-trimethylbenzyl)piperazin-1-yl]-rifamycin SV with a melting point of 203°–204° C.

$C_{61}H_{83}N_3O_{16}$; mol. wt.: 1081 (found, MS)

EXAMPLE 2

Solid tetrabutylammonium fluoride trihydrate is added in portions at room temperature, while stirring, to a solution of 10.7 g of the target product of Example 1 in 200 ml of tetrahydrofuran until the initial red colour of the solution has changed to yellow. After the addition of water and acidification with citric acid, the reaction product is taken up in ethyl acetate. The ethyl acetate extract is washed with water and a solution of sodium chloride, dried over sodium sulfate and concentrated by evaporation under vacuum. The residue is crystallised from ether yielding 1-deoxy-15-deoxo-1,15-oxy-3-[4-(2,4,6-trimethylbenzyl)piperazin-1-yl]-rifamycin of formula I in which $R_1$ is hydrogen, $R_2$ is acetyl and $R_3$ is methyl, in long lemon-yellow prisms which are recrystallised from methanol/water. Melting point: 175° C.

$C_{51}H_{65}N_3O_{11}$; mol. wt.: 895 (found, MS,FD). UV spectrum in 0.01N alcoholic HCl, maxima in nm/ε: 241/37240; 298/23000; 330 (shoulder); 437/9920.

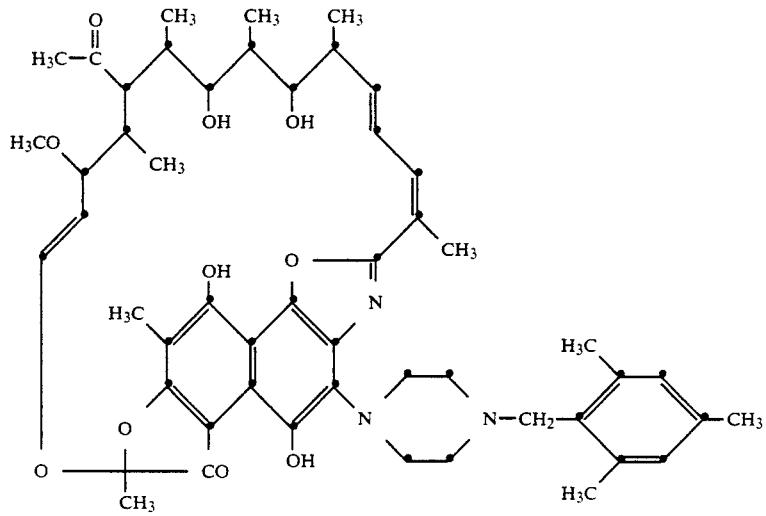

EXAMPLE 3

A solution of the reaction product of Example 2 is allowed to stand at room temperature for 21 hours in dioxane/1N sodium hydroxide solution (1:1). After dilution with water and acidification with citric acid, the reaction product is taken up in ethyl acetate and crystallised from ethyl acetate/ether, yielding 25-deacetyl-3-[4-(2,4,6-trimethylbenzyl)piperazin-1-yl]-1-deoxy-15-deoxo-1,15-oxy-rifamycin of formula I in which $R_1$ is hydrogen, $R_2$ is hydrogen and $R_3$ is methyl, in the form of yellow crystals having a melting point of 190°–195° C. (decomposition).

$C_{49}H_{63}N_3O_{10}$; mol. wt.: 853 (found, MS, FD).

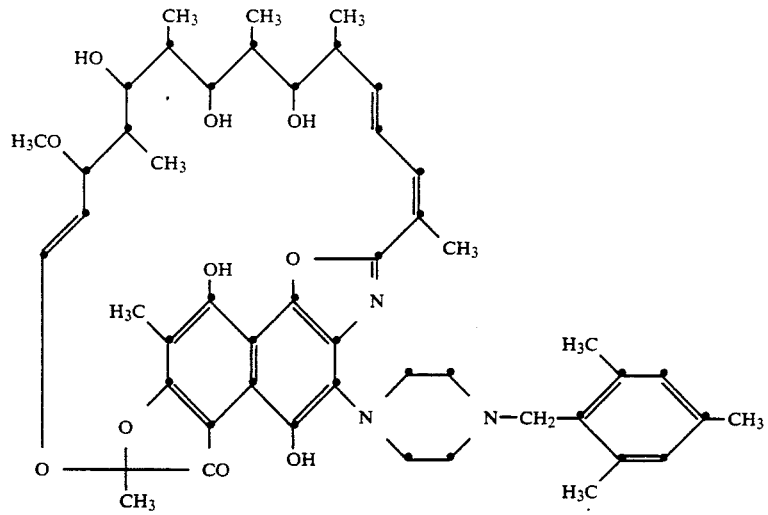

EXAMPLE 4

10 equivalents of pivaloyl chloride are added to a solution of the target product described in Example 3 in pyridine and the mixture is allowed to stand at room temperature until analysis by thin-layer chromatography shows that no more starting material can be detected in the reaction product. The reaction mixture is then rapidly concentrated to dryness by evaporation under a high vacuum and the residue is taken up in methylene chloride. The methylene chloride extract is washed in succession with a solution of citric acid, a buffer solution of pH 7, and a saturated solution of sodium chloride. The methylene chloride extract is dried and concentrated by evaporation 4-(2,4,6-trimethylbenzyl)piperazin-1-yl]-1-deoxy-15-deoxo-1,15-oxy-rifamycin of formula I in which $R_1$ is pivaloyl, $R_2$ is hydrogen and $R_3$ is methyl.

$C_{54}H_{71}N_3O_{11}$; mol. wt.: 937 (found, MS,FD). $^1$H-NMR (CDCl$_3$, 360 MHz): signal of the pivaloyl group at 1.41 (s, 9 H, CH$_3$C).

-continued

| Composition (for 1000 capsules): | |
|---|---|
| ethanol | q.s. |

The active ingredient and the corn starch are mixed and the mixture is moistened with a solution of the polyvinyl-pyrrolidone in 50 g of ethanol. The moist mixture is passed through a sieve having a mesh width of 3 mm and dried at 45°. The dry granulate is passed through a sieve having a mesh width of 1 mm and mixed with 5 g of magnesium stearate. The mixture is filled in 0.320 g portions into size 0 dry-fill capsules.

The other compounds prepared according to the

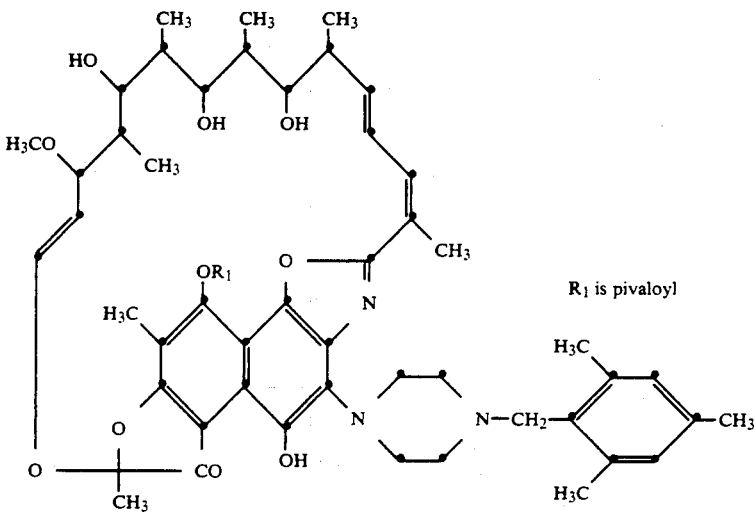

$R_1$ is pivaloyl

EXAMPLE 5

4 g of 8-O,N-dipivaloyl-3-[4-(2,4,6-trimethyl-benzyl)-piperazin-1-yl]-rifamycin S (prepared in accordance with WO 87/02361, Example 1) are heated, with the exclusion of light, in 70 ml of isopropanol in a bomb tube for 4 hours at 100°. The solvent is then removed under vacuum and the dark red residue is chromatographed over 600 g of silica gel (Merck) with petroleum ether/ethyl acetate (3:2). The substances contained in the first two zones are discarded. The red fraction immediately following contains the target product of Example 1. Further target product present in the chromatography column is eluted with ethyl acetate/methanol (9:1) and chromatographed once more for further purification. The eluates are concentrated by evaporation, to give the 8-O-pivaloyl-1-deoxy-15-deoxo-1,15-oxy-3-(2,4,6-trimethylbenzyl)piperazin-1-yl]-rifamycin characterised in Example 1.

EXAMPLE 6

Capsules containing as active ingredient 250 mg of, for example, the compound of formula I in which $R_1$ is pivaloyl, $R_2$ is acetyl and $R_3$ is 2,4,6-trimethylphenyl, can be prepared as follows:

| Composition (for 1000 capsules): | |
|---|---|
| active ingredient | 250.0 g |
| corn starch | 50.0 g |
| polyvinylpyrrolidone | 15.0 g |
| magnesium stearate | 5.0 g |

Examples can also be used as active components in similar manner.

EXAMPLE 7

250 g of an active ingredient according to any one of Examples 1 to 5 and 1750 g of finely triturated suppository base (e.g. cocoa butter) are thoroughly mixed and then the mixture is melted. 1000 suppositories of 2 g are cast from the melt which is kept homogeneous by stirring. Each suppository contains 250 mg of active ingredient.

We claim:

1. A compound of the formula

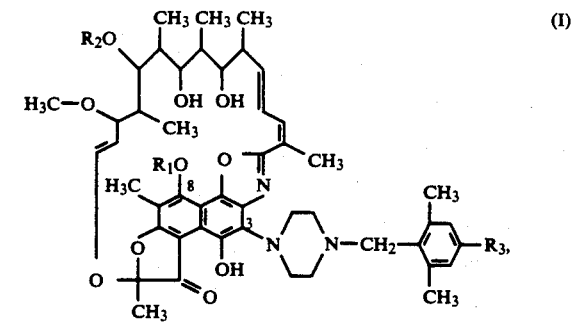

(I)

which is a derivative of rifamycin SV, in which:
 $R_1$ is hydrogen or tri-$C_1$-$C_7$alkylacetyl;
 $R_2$ is hydrogen or acetyl; and
 $R_3$ is $C_1$-$C_7$alkyl;

or a pharmaceutically acceptable salt thereof.

2. A compound according to claim 1 in which $R_1$ is hydrogen or tri-$C_1$-$C_4$alkylacetyl; $R_2$ is hydrogen or acetyl; and $R_3$ is $C_1$-$C_4$alkyl; or a pharmaceutically acceptable salt thereof.

3. A compound according to claim 1 in which $R_1$ is pivaloyl; or a pharmaceutically acceptable salt thereof.

4. A compound according to claim 1 in which $R_3$ is methyl; or a pharmaceutically acceptable salt thereof.

5. A compound according to claim 1 in which $R_1$ is pivaloyl and $R_3$ is methyl; or a pharmaceutically acceptable salt thereof.

6. A compound according to claim 1 in which $R_1$ is hydrogen; $R_2$ is acetyl; and $R_3$ is methyl; or a pharmaceutically acceptable salt thereof.

7. A compound according to claim 1 in which $R_1$ and $R_2$ each are hydrogen; and $R_3$ is methyl; or a pharmaceutically acceptable salt thereof.

8. A compound according to claim 1 in which $R_1$ is pivaloyl; $R_2$ is hydrogen; and $R_3$ is methyl; or a pharmaceutically acceptable salt thereof.

9. 8-O-Pivaloyl-1-deoxo-15-desoxo-1,15-oxy-3-[4-(2,4,6-trimethylbenzyl)]-rifamycin SV of the formula

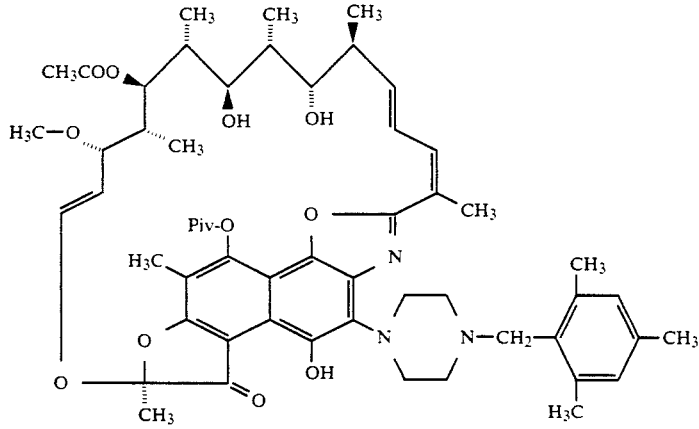

or a pharmaceutically acceptable salt thereof.

10. A pharmaceutical composition suitable for the treatment of hyperlipidemia or arteriosclerosis, which comprises a hyperlipidemically or an antiarteriosclerotically effective amount of a compound according to claim 1 or a pharmaceutically acceptable salt thereof and a carrier.

11. A method for the treatment of hyperlipidemia and arteriosclerosis, which comprises administering to a mammal in need of such treatment a therapeutically effective amount of a compound of the formula

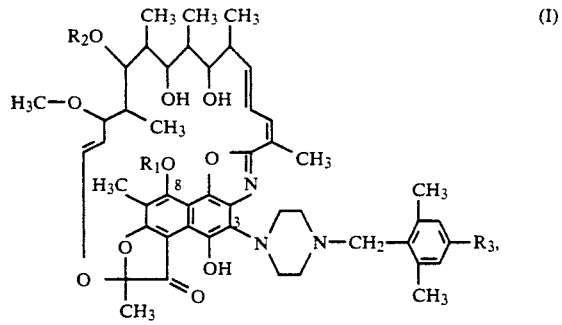

which is a derivative of rifamycin SV, in which:
$R_1$ is hydrogen or tri-$C_1$-$C_7$alkylacetyl;
$R_2$ is hydrogen or acetyl; and
$R_3$ is $C_1$-$C_7$alkyl;
or a pharmaceutically acceptable salt thereof.

* * * * *